US010695388B2

(12) United States Patent
Hsin

(10) Patent No.: US 10,695,388 B2
(45) Date of Patent: Jun. 30, 2020

(54) HIGH MOLECULAR WEIGHT POLYMERIC COMPOSITION AND A NEW USAGE OF THE HIGH-MOLECULAR WEIGHT POLYMERIC COMPOSITION

(71) Applicant: Shao Chi Hsin, New Taipei (TW)

(72) Inventor: Shao Chi Hsin, New Taipei (TW)

( * ) Notice: Subject to any disclaimer, the term of this patent is extended or adjusted under 35 U.S.C. 154(b) by 0 days.

(21) Appl. No.: 13/920,554

(22) Filed: Jun. 18, 2013

(65) Prior Publication Data

US 2013/0280292 A1 Oct. 24, 2013

Related U.S. Application Data

(63) Continuation-in-part of application No. PCT/CN2012/071184, filed on Feb. 16, 2012.

(51) Int. Cl.
| | | |
|---|---|---|
| *A61K 36/72* | (2006.01) | |
| *A61K 36/00* | (2006.01) | |
| *A61K 36/185* | (2006.01) | |
| *A23L 33/28* | (2016.01) | |
| *A23L 33/24* | (2016.01) | |
| *A23L 33/21* | (2016.01) | |

(52) U.S. Cl.
CPC ............ *A61K 36/185* (2013.01); *A23L 33/21* (2016.08); *A23L 33/24* (2016.08); *A23L 33/28* (2016.08); *A23V 2002/00* (2013.01)

(58) Field of Classification Search
CPC ............................ A61K 2300/00; A61K 45/06
USPC ......................................... 424/725, 400, 439
See application file for complete search history.

(56) References Cited

U.S. PATENT DOCUMENTS

| | | | |
|---|---|---|---|
| 2004/0259899 A1 | 12/2004 | Sanghvi et al. | |
| 2008/0063645 A1 | 3/2008 | Terato et al. | |
| 2008/0095881 A1 | 4/2008 | Ber | |

FOREIGN PATENT DOCUMENTS

| | | | |
|---|---|---|---|
| CN | 1235832 A | | 11/1999 |
| CN | 1308899 | | 8/2001 |
| CN | 1806700 | | 7/2006 |
| CN | 101548757 A | | 10/2009 |
| CN | 201710674 | | 1/2011 |
| CN | 102138645 A | * | 8/2011 |
| EP | 1000615 | | 11/2004 |
| JP | 08109178 A | * | 4/1996 |
| JP | 2008-1829 | | 1/2008 |
| JP | 2008-529981 | | 8/2008 |
| KR | 2008-0035729 | | 4/2008 |
| WF | WO2004041254 | | 5/2004 |
| WO | WO 94/16714 | | 8/1994 |
| WO | WO 02/40039 | | 5/2002 |
| WO | WO 2009/027985 | | 3/2009 |
| WO | WO 2009/100181 | | 8/2009 |
| WO | WO 2010-059725 | | 5/2010 |
| WO | WO 2010/059725 | | 5/2010 |

OTHER PUBLICATIONS

Document entitled 'Normacol Plus Product Information', 2-pages, Jan. 2011).*
Document entitled Normacol Plus Product Information, 2-pages, Jan. 2011) (Year: 2011).*
Office action with a search report dated May 30, 2016 for the Taiwan counterpart application 100100360.
English translation of the office action dated May 30, 2016 for the Taiwan counterpart application 100100360.
English translation of the search report dated May 30, 2016 for the Taiwan counterpart application 100100360.
"Normacol plus (sterculia, frangula)", Jan. 27, 2009.
"Normacol Plus Granules (sterculia, frangula)", Jan. 25, 2010.
English translation of the relevant passage of "Normacol Plus Granules (sterculia, frangula)", Jan. 25, 2010.
Office action with a search report dated May 30, 2016 for the Chilean counterpart application 2360-2013.
English abstract translation of CN 1806700.
English abstract translation of CN 1308899.
Supplementary European Search Report, dated Apr. 24, 2017 for the EPO counterpart application No. EP 12747509.
English translation of CN 201710674.
China office action dated Apr. 27, 2016 for counterpart China application 201280008049.0.
English abstract translation of the China office action dated Apr. 27, 2016 for counterpart China application 201280008049.0.
Colombia office action dated Dec. 22, 2016 for counterpart Colombia application 13-215967.
Dr. José M$^a$ Suñé Negre, "Nuevas aportaciones galénicas a las formas de administración", 2001.
English abstract translation of the office action and WO 94/16714 and Nuevas aportaciones galénicas a las formas de administración.
Japan office action dated Oct. 22, 2015 for counterpart Japan application 2013-553775.
English translation of JP 2008-1829.
English translation of JP 2008-529981.
English abstract translation of the Japan office action dated Oct. 22, 2015 for counterpart Japan application 2013-553775.

(Continued)

*Primary Examiner* — Michael Barker
*Assistant Examiner* — Randall Winston
(74) *Attorney, Agent, or Firm* — WPAT, P.C., Intellectual Property Attorneys; Anthony King

(57) ABSTRACT

Approach is provided for a high molecular weight polymeric composition and a new usage of the high-molecular weight polymeric composition. The new usage of the high-molecular weight polymeric composition directly adsorbs body fluid, or indirectly adsorbs toxin or stimulating substance existed in the intaked solution or liquid and removes the body fluid or the toxin or stimulating substance out of body. Therefore, the high-molecular weight polymeric composition is helpful to reduce the food digestibility or to prevent the toxin or stimulating substance from adsorbing in the gastrointestinal tract, even to bring the toxin or stimulating substance out of the body. Accordingly, the high-molecular weight polymeric composition is able to be applied to control weight by lowering the food digestibility or avoid damage by decreasing the toxin or stimulating substance released into the body. The high molecular weight polymeric composition has well biocompatibility to be widely applied in human.

3 Claims, 1 Drawing Sheet

(56) References Cited

OTHER PUBLICATIONS

New Zealand office action dated Sep. 16, 2014 for counterpart New Zealand application 614587.
Conti, Matteo, et al. "Anticancer drug delivery with nanoparticles." In Vivo 20.6A (2006): 697-701.
Russia office action dated Sep. 24, 2015 for counterpart Russia application 2013142189.
English translation of the Russia office action dated Sep. 24, 2015 for counterpart Russia application 2013142189.
Polysorbovit by Ju.s.Khotimchenko, M.V.Odintsova, V.V.Kovalev.
English translation of Polysorbovit by Ju.s.Khotimchenko, M.V. Odintsova, V.V.Kovalev.
Office Action along with a Search Report and Examination report, dated Jun. 5, 2017, Jul. 3, 2017 for the United Arab Emirates counterpart application No. 883/2013.
Office Action for corresponding Korean application 10-2013-7023947 dated Apr. 20, 2018.
English translation of the Office Action for corresponding Korean application 10-2013-7023947 dated Apr. 20, 2018.
Tripathi, Dulal Krishna. 2018. Pharmaceutics: Basic Principles and Formulations.
New Zealand Minister of Health. 1957. The Drug Tariff 1957.
Netdoctor.com. <https://www.netdoctor.co.uk/medicines/digestion/a7234/normacol-plus-sterculia-frangula/> Normacol plus (sterculia, frangula). Jan. 27, 2009.
Prepared at the 33rd JECFA (1988), published in FNP 38 (1988) and in FNP 52 (1992). "Karaya Gum".
Herbal Medicines, 3rd Ed, Barnes-Anderson-Phillipson, 2007: Herbal Medicines by Pharmaceutical Press-Royal Pharmaceutical (p. 270-272).

* cited by examiner

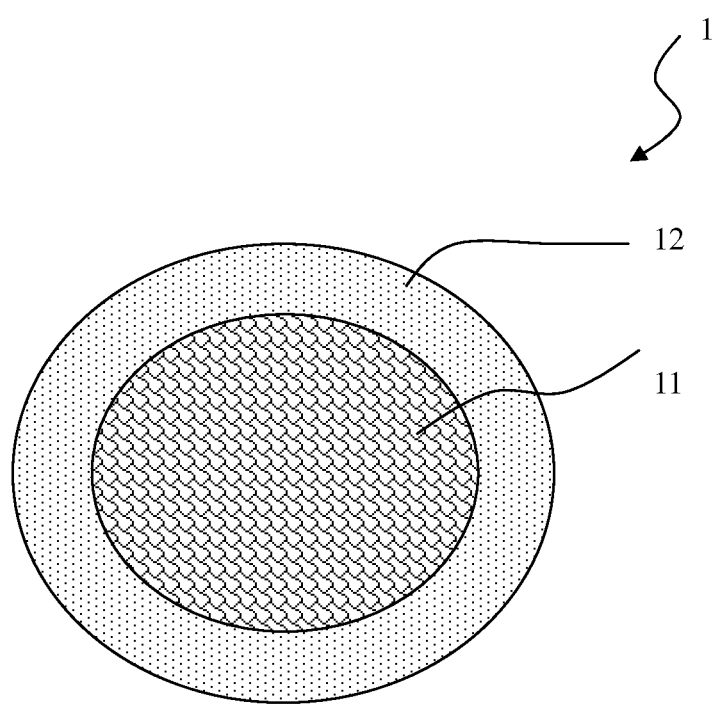

HIGH MOLECULAR WEIGHT POLYMERIC COMPOSITION AND A NEW USAGE OF THE HIGH-MOLECULAR WEIGHT POLYMERIC COMPOSITION

FIELD OF THE INVENTION

Embodiments of the present invention relate to a high molecular weight polymeric composition and a new usage of the high-molecular weight polymeric composition, especially toward a high-molecular weight polymeric composition has capability to indirectly adsorb and remove body fluid, liquid or solution ingested from food, or harmful or toxic substances existed in food and a new usage of the high molecular weight polymeric composition.

BACKGROUND

A conventional high molecular weight polymer includes a natural polymeric composition, such as an animal source of a collagen, a gelatin, a hyaluronic acid, a chitin, a chitosan or a derivative of above mention composition or a plant source of an alginates, a cellulose or a derivative of above mention composition, has excellent biocompatibility and bio-degradability, is divided into small molecules in an organism, and is removed out of the body through a kidney filtering and metabolizing.

Those high molecular weight polymers and relative compositions might be used as a food additive due to well swelling property to increase full sense, decrease dietary requirement and achieve the purpose of sliming down the weight. Moreover, the high molecular weight polymers and relative compositions comprise a lot of fiber to improve the movement of the gastrointestinal tract to be a major gradient of a stool softener (i.e. Sterculia BP or Frangula BPC) and promote the defecation of a constipated patient.

However, above mentioned applications of the high molecular weight polymers and relative compositions are focused on the water adsrobability of the high molecular weight polymers and relative compositions, ignore other developing potential and lower the actually industrial value.

SOME EXEMPLARY EMBODIMENTS

These and other needs are addressed by the invention, wherein approaches are provided for a high molecular weight polymeric composition and a new usage of the high-molecular weight polymeric composition.

According to one aspect of an embodiment of the invention, the new usage of a high-molecular weight polymeric composition being adsorbed a toxin or a stimulating substance existed in a solution that is intaked into the body and removing the toxin or the stimulating substance out of the body to prevent the body from being damaged by the toxin or the stimulating substance.

According to another aspect of an embodiment of the invention, the high-molecular weight polymeric composition comprises a high-molecular weight polymer, and a biocompatibility excipient combined with the high-molecular weight polymer. The high-molecular weight polymer has capability to adsorb a toxin or a stimulating substance existed in a solution that is intaked into the body and removed the toxin or the stimulating substance out of the body to prevent the body from being damaged by the toxin or the stimulating substance.

Accordingly, the high-molecular weight polymeric composition is able to be applied to control weight by lowering the food digestibility or avoid damage by decreasing the toxin or stimulating substance released into the body. The high molecular weight polymeric composition has well biocompatibility to be widely applied in human.

BRIEF DESCRIPTION OF THE DRAWINGS

The invention is illustrated by way of example, and not by way of limitation, in the FIGURES of the accompanying drawings in which like reference numerals refer to similar elements and in which:

FIG. 1 is a cross-sectional view of a high molecular weight polymeric composition in accordance with the present invention.

DESCRIPTION OF THE PREFERRED EMBODIMENT

In the following description, for purposes of explanation, numerous specific details are set forth in order to provide a thorough understanding of the embodiment of the invention. It is apparent, however, to one skilled in the art that the present invention may be practiced without these specific details or with an equivalent arrangement. Same element in various embodiments of the present invention may use same numbering in different illustrated FIGURES.

A high molecular weight polymeric composition and a new usage of the high-molecular weight polymeric composition. In the following description, for the purposes of explanation, numerous specific details are set forth in order to provide a thorough understanding of the present invention. It is apparent, however, to one skilled in the art that the invention may be practiced without specific details or with an equivalent arrangement. In other instances, well-known structures and devices are shown in block diagram form in order to avoid unnecessarily obscuring the embodiments of the present invention.

In one embodiment, the new usage of the high-molecular weight polymeric composition adsorbs a body fluid of an organism (i.e. digestion fluid), toxin existed in the organism, or a liquid or a solution containing a stimulating or a harmful substance, thus, the body fluid, the liquid or the solution is directly by inhaled inside the high-molecular weight polymeric composition and the toxic or the harmful substance is indirectly grabed by the high-molecular weight polymeric composition. Accordingly, fewer body fluid is applied to digest the intaked food to reduce the assimilate efficiency of food, and less toxin or harmful substance in the food or drink directly contact with the digestion organs/tissues to avoid the health damages due to adsorb excess toxin or harmful substance. In this embodiment, the high-molecular weight polymeric composition is applied to adsorb solutions including body fluid, liquids intaked into or existed in the body, therefore, the toxic or harmful substances in the solutions also grabed by the high-molecular weight polymeric composition and removed out of the body wile defecating. Because the water adsorption is The high-molecular weight polymeric composition is selected from the group consisting of: a high-molecular weight fiber, natural fiber, symthetic fiber, and high molecular weight absorber. The natural fiber is selected from the group consisting of: Sterculia BP, Frangula BPC, collagen, cellulose, chitin and chitosan. The high-molecular weight polymeric composition has excellent biocompatibility, has a high reticulate structure, and forms mutilple tiny apertures with different sizes. Therefore, the high-molecular weight polymeric composition will not damage the health after being intaked into the body. Further, toxin or stimulating components existed in the food or drink will be adsorbed and fixed in the apertures to avoid the toxin or stimulating components from contacting with the tissues and generating the damage to the tissues.

Example 1

In this example, a Sterculia BP is selected to adsorb a coffee solution to illustrate the new usage of the high-molecular weight polymeric composition of the present invention. The Sterculia BP is a kind of high molecular fiber, is applied sinlely or mixed with another adsorptive material. In this example, The Sterculia BP is mixed with a Frangula BPC by 25% and 75% of percentage weight to from a high molecular weight fiber mixture. One gram of fiber mixture is added into 30 ml espresso coffee to be mixed well and form a fiber-coffee mixture. After 5 minutes, the fiber-coffee mixture is getting stringy. After 10 minutes, the fiber-coffee mixture performances as semi-solid state and is still getting thicken. After 30 minutes, the fiber-coffee mixture is almost solidify and lacks most flow property. In this example, people intaked the fiber mixture before drinking the espresso coffee, the caffeine in the coffee is grabed by the fiber mixture through the adsorption of espresso coffee. Therefore, most caffeine is isolated with the digestion tissue to efficient reduce the health damage result from the caffeine.

The mix rate of Sterculia BP and Frangula BPC is not limited as 25% and 75%. The Sterculia BP might be applied single or be mixed with any other high molecular weight polymer.

Example 2

A common drink cola is applied in this example to illustrate the new usage of the high-molecular weight polymeric composition of the present invention. The Sterculia BP is mixed with a Frangula BPC by 25% and 75% of percentage weight to from a high molecular weight fiber mixture. One gram of fiber mixture is added into 30 ml cola to be mixed well and form a fiber-cola mixture. After 5 minutes, the fiber-cola mixture is getting stringy. After 10 minutes, more than 95% of cola is adsorbed by the high-molecular weight polymeric composition and the fiber-cola mixture almost lacks the flow property. After 30 minutes, the fiber-cola mixture is solidity. Therefore, the high-molecular weight polymeric composition is able to quickly keep and adsorb the flow though cola and grab any harmful substance to protect the body from contacting and digesting the harmful substance.

Example 3

This example uses the high-molecular weight polymeric composition same as example to adsorb an alcohol solution to illustrate the new usage of the high-molecular weight polymeric composition of the present invention. One gram high molecular weight polymeric composition is added in 30 ml sorghum wine containing 58% alcohol to form a fiber-wine mixture. The fiber-wine mixture is getting stringy after 5 minutes mixing, performances as a gel after 10 minutes mixing, and becomes a fiber-wine cake after 20~30 minutes mixing. After one hour, the fiber-wine mixture is solidity and loses the flow property. Accordingly, the high-molecular weight polymeric composition of the present invention has capability to adsorb the intaked alcohol and prevent the alcohol directly contacting the tissue and generating health damage.

In one test, the alcohol concentration in blood of a person administrated 5 grams high-molecular weight polymeric composition before drinking the sorghum wine (Experiment Group) is obviously lower than a person did not administrate the high-molecular weight polymeric composition (Control Group) (shown as Table. 1) in the sampling process. In the experiment group, most alcohol is blocked by the high-molecular weight polymeric composition and only a few alcohols enter into the blood from the beginning of sampling. However, the alcohol concentration in blood keeps increasing to one hour which is two times of the 10 minutes sampling after drinking the sorghum wine in the control group. Therefore, it is obviously that the high-molecular weight polymeric composition is efficient to avoid the toxin (i.e. alcohol) entering the blood and damaging the tissues.

TABLE 1

The alcohol content in blood of a person administrated 5 grams high-molecular weight polymeric composition before drinking the *sorghum* wine containg 58% alcohol.

| | Alcohol concentration in blood (mg/dl) | |
|---|---|---|
| Sampling Time (min) | Control Group | Experiment Group |
| 10 | 0.044 | 0.030 |
| 30 | 0.061 | 0.041 |
| 45 | 0.098 | 0.050 |
| 60 | 0.101 | 0.051 |

In another test, the alcohol concentration in blood of a person administrated 5 grams high-molecular weight polymeric composition before drinking the Brandy (Experiment Group) is obviously lower than a person did not administrate the high-molecular weight polymeric composition (Control Group) (shown as Table. 2) in the sampling process. In the experiment group, most alcohol is blocked by the high-molecular weight polymeric composition and only a few alcohols enter into the blood from the beginning of sampling. However, the alcohol concentration in blood keeps increasing to one hour which is two times of the 10 minutes sampling after drinking the Brandy in the control group. Therefore, it is obviously that the high-molecular weight polymeric composition is efficient to avoid the toxin (i.e. alcohol) entering the blood and damaging the tissues.

TABLE 2

The alcohol content in blood of a person administrated 5 grams high-molecular weight polymeric composition before drinking the Brandy containing 40% alcohol.

| | Alcohol concentration in blood (mg/dl) | |
|---|---|---|
| Sampling Time (min) | Control Group | Experiment Group |
| 5 | 0.046 | 0.020 |
| 10 | 0.047 | 0.030 |
| 20 | 0.076 | 0.027 |
| 30 | 0.102 | 0.026 |

Moreover, when one gram Sterculia BP is added into 50 ml sorghum wine containg 58% alcohol, the Sterculia BP gradually adsorbs the sorghum wine and presents as a semi-flow gel, cake and solid block. The fiber-wine mixture is getting stringy after 5 minutes mixing, and presents as a gel after 10 minutes mixing. Finally, the fiber-wine mixture becomes a cake and a solid after 20~30 minutes and one hour mixing respectively. Therefore, the harmful alcohol is intaked into the gastrointestinal tract and immediately grabbed by the high-molecular weight polymeric composition to reduce the direct contacting amount of the alcohol with the tissues and avoid generating health damage.

The high-molecular weight polymeric composition is manufactured as a chew that is intaked before drinking and participating a party or a banquet. The intaked alcohol is immediately grabbed by the high-molecular weight polymeric composition stayed in the gastrointestinal tract to reduce the contacting and digesting amount of the alcohol and decrease the damage degree of the body. Moreover, the high-molecular weight polymeric composition is applied in adsorbing stimulating substance such as caffeine, drug or tea extract to assist to withdraw the addiction about the caffeine, drug or tea extract. Further, the high-molecular weight polymeric composition of the present invention is able to adsorb acid or alkali and is applied to decrease uncomfortable due to eat strong acid/alkali by mistake or excess secret of stomach fluid.

The high-molecular weight polymeric composition in this embodiment is mixed with a biocompatibility excipient to form a pill, a tablet, a capsule, a micro particle, a emulsion or an injection that are injected, spread, oral administrated or sprayed to the body. With reference to FIG. 1, high-molecular weight polymeric composition of the embodiment is manufactured as a pill 1 and comprises a high-molecular weight polymeric core 11 and a shell 12. The shell 12 is disposed outside of the high-molecular weight polymeric core 11 and is made of at least one biocompability biocompatibility excipient and comprises multiple holes. The toxin or the stimulating substance gets into the pill and is fixed between fibers of high-molecular weight polymeric core 11 within the high-molecular weight polymeric core 11

Accordingly, the high-molecular weight polymeric composition promptly receives and adsorbs the toxin or stimulating substance existed in the liquid or solution to avoid the harmful toxin or stimulating substance from directly contacting to the tissue to reduce the toxicity, damage degree and side affection. The new usage of the high-molecular weight polymeric composition is to directly adsorb the intaked solution or liquid to indirectly garb the harmful substance and toxin existed in the solution or liquid that is removed out of the body with the high-molecular weight polymeric composition. Therefore, the application field of the high-molecular weight polymeric composition is wider to improve the commercial potential.

While the invention has been described in connection with a number of embodiments and implementations, the invention is not so limited but covers various obvious modifications and equivalent arrangements, which fall within the purview of the appended claims. Although features of the invention are expressed in certain combinations among the claims, it is contemplated that these features can be arranged in any combination and order.

What is claimed is:

1. A method for the absorption of a toxin or a harmful substance in a liquid or solution intaked into the body, comprising the steps of:
    administrating a high molecular weight polymeric composition to the body, wherein said composition comprises:
        a high molecular weight polymeric core comprising 25% by weight of Sterculia BP and 75% by weight of Frangula BPC; and
        a shell disposed outside of the high-molecular weight polymeric core and comprising a biocompatible excipient; and
    intaking the liquid or solution containing the toxin or the harmful substance into the body;
        wherein the high molecular weight polymeric core is present in the composition in an amount sufficient to convert the liquid or solution intaked into the body to a semi-solid to solid colloid;
        wherein the shell comprises multiple holes; and
        wherein the toxin or harmful substance is acid, alcohol, caffeine, base, theine or uric acid.

2. The method of claim 1, wherein 1 g of the high molecular weight polymeric core is used to absorb 30 ml to 50 ml of the liquid or solution.

3. The method of claim 1, wherein the colloid formed is removed from the body by excretion.

\* \* \* \* \*